(12) United States Patent
Kostromine et al.

(10) Patent No.: US 9,604,943 B2
(45) Date of Patent: *Mar. 28, 2017

(54) UV ABSORBER-CONTAINING URETHANE ACRYLATE

(71) Applicant: Bayer MaterialScience AG, Monheim am Rhein (DE)

(72) Inventors: Serguei Kostromine, Swisttal (DE); Joachim Petzoldt, Monheim (DE); Wolfgang Fischer, Meerbusch (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/763,897

(22) PCT Filed: Jan. 27, 2014

(86) PCT No.: PCT/EP2014/051489
§ 371 (c)(1),
(2) Date: Jul. 28, 2015

(87) PCT Pub. No.: WO2014/118116
PCT Pub. Date: Aug. 7, 2014

(65) Prior Publication Data
US 2015/0368212 A1    Dec. 24, 2015

(30) Foreign Application Priority Data
Feb. 1, 2013  (EP) .................... 13153700

(51) Int. Cl.
*C07D 251/22* (2006.01)
*C07D 251/24* (2006.01)
*C08G 18/81* (2006.01)
*C09D 175/16* (2006.01)
*C08G 18/38* (2006.01)
*B05D 3/06* (2006.01)
*C09D 5/32* (2006.01)
*C09D 133/14* (2006.01)

(52) U.S. Cl.
CPC ......... *C07D 251/24* (2013.01); *B05D 3/067* (2013.01); *C07D 251/22* (2013.01); *C08G 18/3851* (2013.01); *C08G 18/81* (2013.01); *C08G 18/8175* (2013.01); *C09D 5/32* (2013.01); *C09D 133/14* (2013.01); *C09D 175/16* (2013.01)

(58) Field of Classification Search
CPC .............................. C07D 251/24; C08G 18/81
USPC ........................... 544/180; 252/589; 427/379
See application file for complete search history.

(56) References Cited

U.S. PATENT DOCUMENTS 5,097,002 A   3/1992  Sakashita et al.
5,288,778 A   2/1994  Schmitter et al.
5,340,905 A   8/1994  Kühling et al.
5,717,057 A   2/1998  Sakashita et al.
6,225,384 B1  5/2001  Renz et al.
6,596,840 B1  7/2003  Kratschmer et al.
(Continued)

FOREIGN PATENT DOCUMENTS

DE       4 238 123 A1    5/1994
DE    102006016642 A1   10/2007
(Continued)

OTHER PUBLICATIONS

International Search Report for PCT/EP2014/051489 mailed Feb. 26, 2014.

*Primary Examiner* — Venkataraman Balasubramanian
(74) *Attorney, Agent, or Firm* — Drinker Biddle & Reath LLP

(57) ABSTRACT

The present invention relates to a UV absorber-comprising urethane acrylate, to a process for its preparation, and to the use thereof. The UV absorber is chemically bonded into the system. The UV absorber-comprising urethane acrylate has the formula (I):

(Formula I)

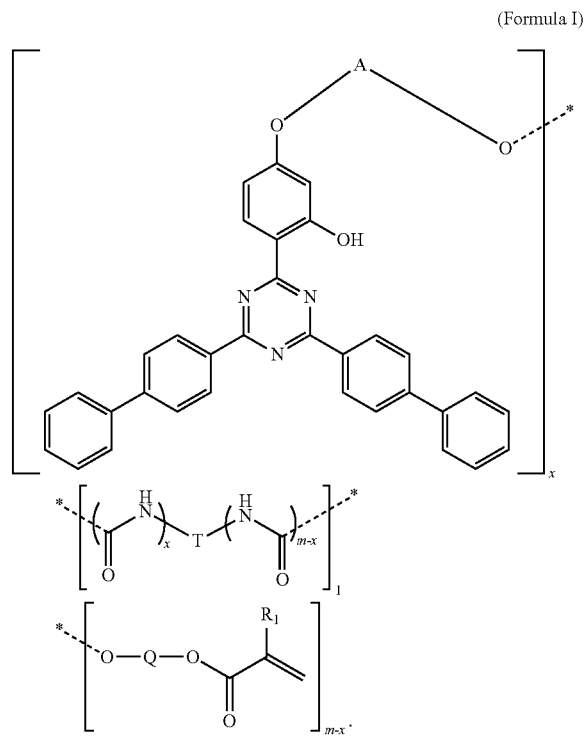

15 Claims, No Drawings

(56) References Cited

U.S. PATENT DOCUMENTS

| | | | |
|---|---|---|---|
| 6,740,730 | B1 | 5/2004 | Kratschmer et al. |
| 7,071,284 | B2 | 7/2006 | Kauth et al. |
| 7,442,430 | B2 | 10/2008 | Buckel et al. |
| 8,753,739 | B2 | 6/2014 | Buckel et al. |
| 9,273,213 | B2 * | 3/2016 | Kostromine ............ C07B 63/04 |
| 2012/0094127 | A1 | 4/2012 | Meyer zu Berstenhorst et al. |
| 2012/0262664 | A1 | 10/2012 | Kues et al. |
| 2013/0236743 | A1 | 9/2013 | Kostromine et al. |

FOREIGN PATENT DOCUMENTS

| | | |
|---|---|---|
| DE | 10 2009 032 921 A1 | 1/2011 |
| EP | 0 500 496 A1 | 8/1992 |
| EP | 1308084 A1 | 5/2003 |
| WO | WO-99/55772 A1 | 11/1999 |
| WO | WO-00/66675 A1 | 11/2000 |
| WO | WO-0105866 A1 | 1/2001 |
| WO | WO-0105867 A1 | 1/2001 |
| WO | WO-2004/063249 A1 | 7/2004 |
| WO | WO-2006/108520 A1 | 10/2006 |
| WO | WO-2011006552 A1 | 1/2011 |
| WO | WO-2012049091 A1 | 4/2012 |

* cited by examiner

UV ABSORBER-CONTAINING URETHANE ACRYLATE

CROSS-REFERENCE TO RELATED APPLICATIONS

This application is a national stage application (under 35 U.S.C. §371) of PCT/EP2014/051489, filed Jan. 27, 2014, which claims benefit of European Application No. 13153700.3, filed Feb. 1, 2013, both of which are incorporated herein by reference in their entirety.

The present invention relates to a UV absorber-comprising urethane acrylate, to a process for its preparation, and to the use thereof. The UV absorber is chemically bonded into the system.

For outside applications, transparent plastics articles, such as, for example, sheets, films or extruded mouldings, must be protected especially by means of UV protection against aggressive solar radiation and by means of a scratch-resistant finish against mechanical action. A common method for that purpose is to provide the upper, and sometimes also the only, protective layer, which must be scratch-resistant, with an additional UV protection function and to equip it to that end with a substantial amount of UV absorbers (see DE-A 10 2006 016 642). Conventional UV absorbers, however, act as plasticisers in the protective layers and reduce the mechanical resistance of the layer.

Typical UV absorber classes are, for example, biphenyl-substituted triazines (see WO-A 2006/108520). This substance class exhibits an outstanding absorption effect at 320-380 nm and at the same time a very high intrinsic UV stability (WO 2000/066675 A1, U.S. Pat. No. 6,225,384).

The influence of the UV absorber on the mechanical and chemical resistance of the coating is all the greater, the higher the concentration thereof in the coating. However, certain concentrations of the absorber are required in order to absorb UV light effectively and protect the substrate therefrom reliably and permanently. According to Lambert's law, that concentration will be higher, the thinner the coating. For modern film coatings, the layer thickness of which can be between 1 and 10 µm, this means that they are to comprise up to 10 wt. % of the UV absorber in order to exhibit the necessary absorbing power. However, the mechanical and chemical resistance of such coatings could be adversely affected thereby.

A possible solution to the problem might be for the UV absorber not to be present as a passive additive but to play an active part chemically in the curing process and to be incorporated into the polymer framework of the coating.

The object of the present invention is to provide such UV absorbers and a process for their preparation. In summary, the object has been achieved by chemically bonding UV absorbers from the class of the biphenyl-substituted s-triazines to the structure of urethane acrylate resins.

The object has been achieved according to the invention by a UV absorber-comprising urethane acrylate of formula (I)

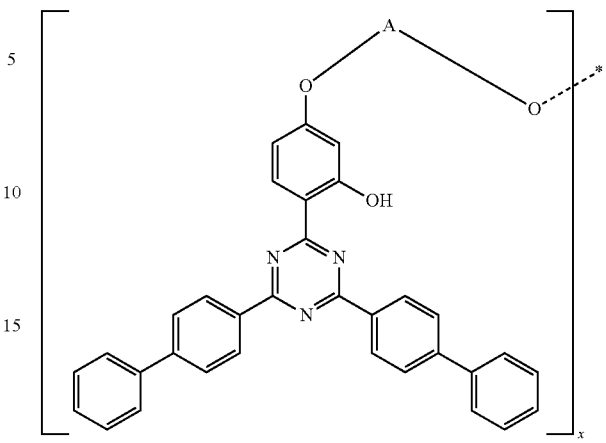

(Formula I)

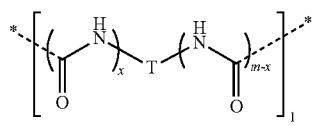

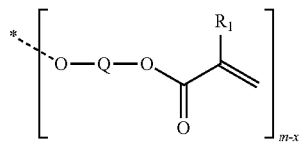

wherein $R_1$ is a hydrogen or a methyl radical,

Q is a linker of the commercially available hydroxyalkyl (meth)acrylate from the group 2-hydroxyethyl (meth)acrylate, 2-hydroxypropyl (meth)acrylate, 4-hydroxybutyl (meth)acrylate, 3-hydroxy-2,2-di-methylpropyl(meth)acrylate, T is a nucleus of the commercially available aliphatic and cycloaliphatic polyisocyanates $T(NCO)_m$ which have cyclic isocyanurate, uretdione, iminooxadiazinedione or oxadiazinetrione structures, as well as branched biuret structures in the case of cycloaliphatic polyisocyanates, m corresponds to the original average NCO functionality of the polyisocyanate used and is equal to or greater than 2, A represents an optionally substituted linear or branched linker of carbon, oxygen, nitrogen, sulfur, phosphorus and/or silicon in the chain, and x represents an average molar amount of the bonded UV absorber radical and is less than m.

Preferably, x is equal to or less than 1.

Within the meaning of the average value of m and x, mixtures of one or more structures of formula (E) with structures of formulae (II) and (III)

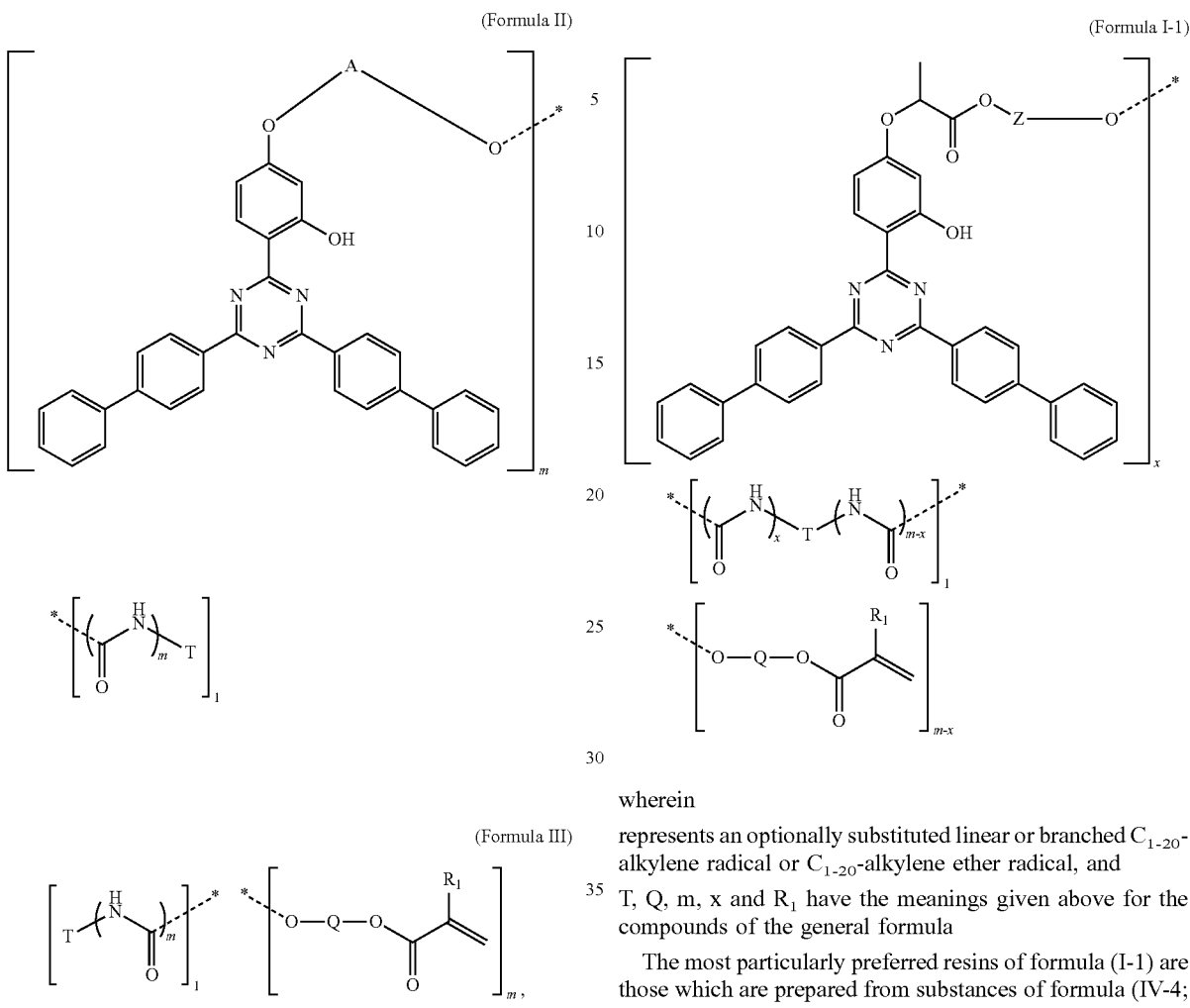

(Formula II)

(Formula III)

the appearance of which in the preparation process of the products of formula (I) cannot be ruled out, is also in accordance with the invention.

The compounds of formula (I) according to the invention preferably exhibit a UV absorption maximum between 300 and 340 nm.

A in the compounds of the general formula (I) preferably represents an optionally substituted linear or branched linker, there being a chain of at least 4 atoms selected from carbon, oxygen, nitrogen, sulfur, phosphorus and/or silicon in the chain between the O atom of the aromatic nucleus of the UV absorber and the O atom of the urethane group.

Embodiments and further aspects of the present invention are described hereinbelow. They can be combined with one another as desired, provided that the contrary is not clearly apparent from the context.

In one embodiment of the UV absorber-comprising urethane acrylate according to the invention, the urethane acrylate has the structure according to formula (I-1):

wherein represents an optionally substituted linear or branched $C_{1-20}$-alkylene radical or $C_{1-20}$-alkylene ether radical, and T, Q, m, x and $R_1$ have the meanings given above for the compounds of the general formula The most particularly preferred resins of formula (I-1) are those which are prepared from substances of formula (IV-4; see below):

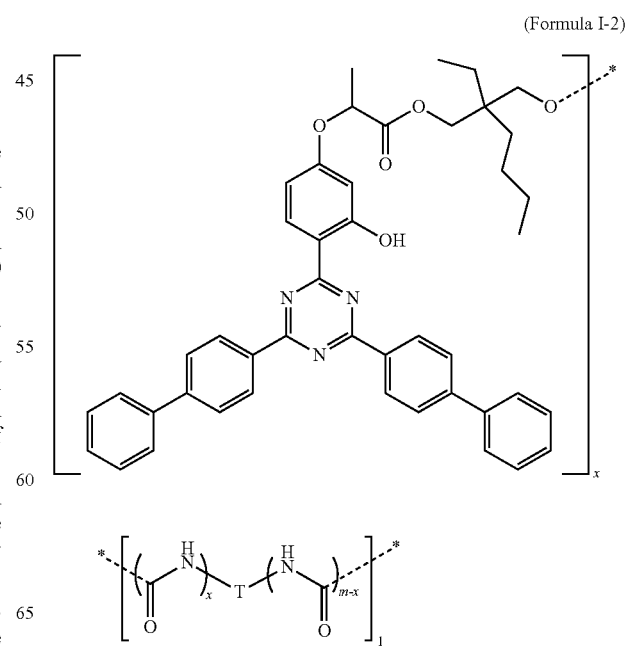

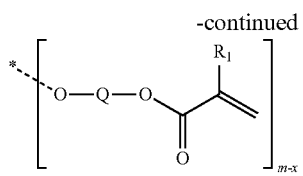

The present invention further provides a process for the preparation of a UV absorber-comprising urethane acrylate, comprising the steps:

a) reacting a compound of the general formula:

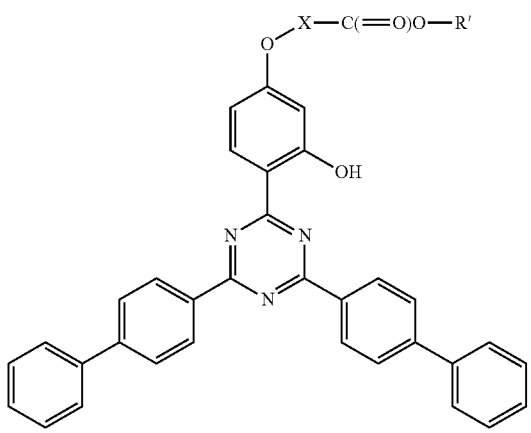

wherein X represents branched or unbranched $C_{1-20}$-alkyl and IV represents branched or unbranched $C_{1-20}$-alkyl, $C_{4-12}$-cycloalkyl, or $C_{6-12}$-aryl optionally substituted by $C_{1-12}$-alkyl, $C_{1-12}$-alkoxy, CN and/or by halogen with an at least difunctional alcohol;

b) reacting the product obtained in step a) with
   bi) an aliphatic or cycloaliphatic, isocyanate group-comprising urethane acrylate which as cyclic isocyanurate, uretdione, iminooxadiazinedione or oxadiazinetrione structures or, in the case of a cycloaliphatic urethane acrylate, can further have branched biuret structures,
   and/or with
   bii) an aliphatic or cycloaliphatic, isocyanate group-comprising polyisocyanate which has cyclic isocyanurate, uretdione, iminooxadiazinedione or oxadiazinetrione structures or, in the case of a cycloaliphatic polyisocyanate, can further have branched biuret structures, wherein the reaction in step h) further takes place in the presence of a hydroxyalkyl (meth)acrylate and/or after the reaction in step b) the resulting product is further reacted with a hydroxyalkyl (meth)acrylate.

In the process according to the invention, it is possible, for example, for a polyisocyanate $T(NCO)_m$ to be reacted with the substance of formula (IV) dissolved in an appropriate solvent:

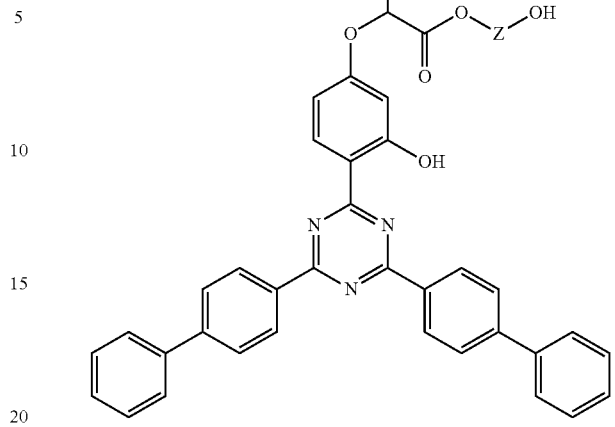

(Formula IV)

wherein Z represents a linear or branched $C_{1-20}$-alkyl or $C_{1-20}$-alkylene ether.

This reaction is continued until the whole of the substance of formula (IV) is bonded to polyisocyanate by urethane groups that form. Hydroxyalkyl (meth)acrylate is then added to the resin in order to allow all the remaining NCO groups of the polyisocyanate to react with OH groups of the hydroxyalkyl (meth)acrylate. At the end of this reaction, the appropriate solvent is added in order to bring the viscosity of the resin to a desired level.

A particular advantage of the process is that the substance of formula (IV) possesses a primary OH group and is able to enter into the reaction with isocyanate groups without a catalyst, in particular without a tin catalyst and most particularly without a dibutyltin dilaurate (DBTL) catalyst. By means of the process according to the invention there are thus formed tin-free, particularly advantageously DBTL-free, products of formula (I).

This distinguishes the process according to the invention from the process of DE 10 2009 032 921 A1 (BASF), where triazine absorbers with secondary OH groups were used. This requires the use of very large amounts of DBTL in the percent range. In addition, it relates only to phenyltriazines and not to particularly advantageous biphenyl-substituted triazines. A further important difference of the process according to the invention is the use of alcohols as solvents for products of formula (I), which renders them particularly advantageous for the coating of polycarbonate. The process of DE 10 2009 032 921 uses MEK, which attacks polycarbonate immediately.

The UV absorbers of the s-triazine class functionalised with an OH group (formula IV) are prepared according to US 2012/0094127 A1 by direct transesterification of Tinuvin 479® (BASF product) with a diol HO—Z—OH.

A further form according to the invention of the preparation process consists in using, instead of the polyisocyanates $T(NCO)_m$, NCO-comprising urethane acrylates (formula V):

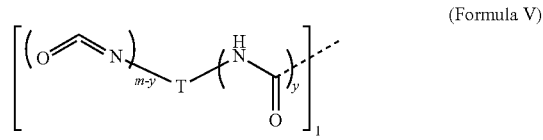

(Formula V)

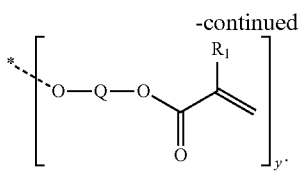

Examples of such products are the NCO-comprising urethane acrylates from Bayer MaterialScience: Desmolux® D100, VP LS 2396 and XP 2510. The process continues as described above.

The substance of formula IV is introduced into the reaction with polyisocyanate in a form which is liquid under the reaction conditions. Three variants come into consideration:

- The substance of formula IV is added to the polyisocyanate in the form of a solution in a further reagent of the process, such as hydroxyalkyl (meth)acrylate. The remaining amount of hydroxyalkyl (meth)acrylate is reacted later as a second step.
- The substance of formula IV is added to the polyisocyanate in the form of a solution in an NCO-neutral solvent. The entire amount of hydroxyalkyl (meth)acrylate is then added to the reaction later as a second step. The fact that the reaction of the NCO group with the OH group proceeds according to the invention without a catalyst permits the use of tertiary alcohols, such as, for example, diacetone alcohol, as solvent (particularly advantageously) for this synthesis.
- The substance of formula IV reacts in the form of a melt with the polyisocyanate. The entire amount of hydroxyalkyl (meth)acrylate is then reacted later as a second step.

The first variant of the process is highly suitable for the preparation of the resin of formula (I) and (I-1) with a relatively small x value (x<0.1), wherein only a relatively small amount of the substance of formula IV is to be dissolved and reacted.

Further variations of the process are connected with the choice of the solvents used and the order in which they are used. The only limitation is that the solvent used (referred to here as solvent of group 1) does not react with isocyanate groups under the process conditions. Typical examples are known to the person skilled in the art. They are aromatic hydrocarbons (toluene), cyclic ethers (THF, dioxane), ketones (acetone, MEK, cyclopentanone) or esters (ethyl and butyl acetate).

The solvents of group 2, which come into the reaction mixture at the end of the process if the resin of formula (I) no longer possesses any free NCO groups, are not subject to the limitations of group 1. Accordingly, group 2 includes all the solvents of group 1 plus all OH-containing solvents known to the person skilled in the art, such as, for example, ethanol, isopropanol, butanol, 1-methoxy-2-propanol, and mixtures thereof.

In one embodiment of the process according to the invention, in step a) in the general formula X represents $CH(CH_3)$.

In a further embodiment of the process according to the invention, in step a) in the general formula R' represents n-octyl or isooctyl.

In a further embodiment of the process according to the invention, in step a) the at least difunctional alcohol is selected from the group 2-butyl-2-ethyl-1,3-propanediol, 2,2-diethyl-1,3-propanediol, 2-methyl-1,3-propanediol and/or 2,2-dimethyl-1,3-propanediol.

In a further embodiment of the process according to the invention, the product obtained from step a) is selected from:

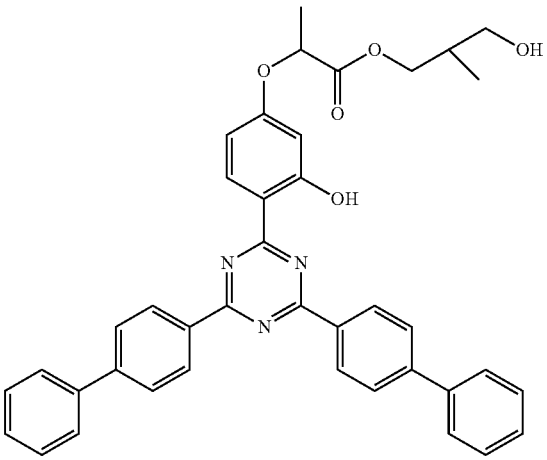

Formula (IV-1)

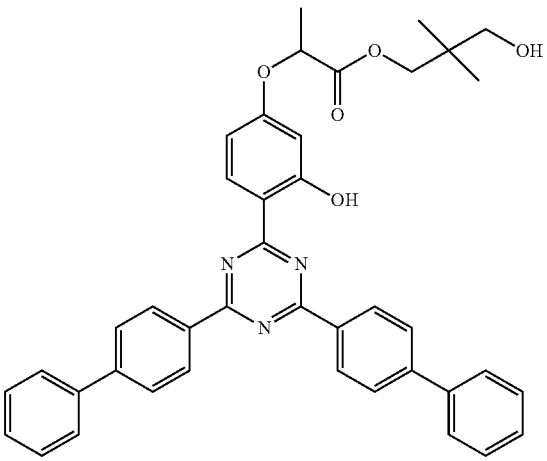

Formula (IV-2)

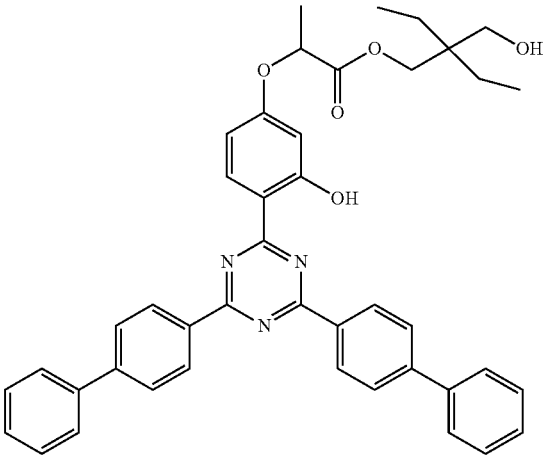

Formula (IV-3)

-continued

Formula (IV-4)

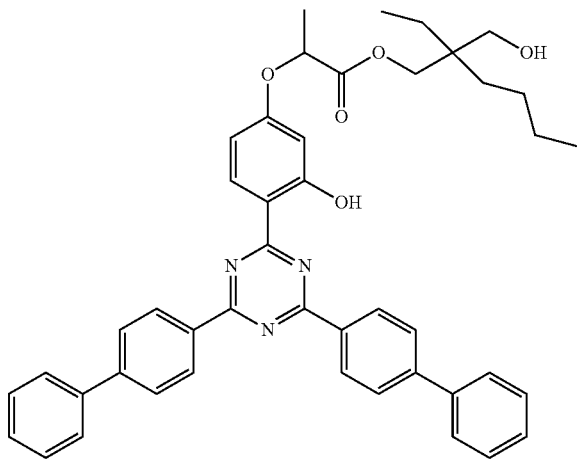

The substances of formulae (IV-1) to (IV-3) are crystalline substances having melting points above 100° C. This makes the use of the solvents of group 1 in the preparation of the resins of formula (I-1) expedient. The fact that the reaction of the NCO groups with the OH groups proceeds according to the invention without a catalyst permits the use of tertiary alcohols, such as, for example, diacetone alcohol, as solvents (particularly advantageously) for this synthesis.

The substance of formula (IV-4) has a melting point of about 80° C. This substance can be present in the form of a melt in the preparation process of the resins of formula (I-1). Solvents of group 1 are not needed in the preparation, which can be regarded as advantageous.

In a further embodiment of the process according to the invention, in step b) the isocyanate group-comprising urethane acrylate is obtainable by reacting a 1,6-hexamethylene diisocyanate isocyanurate with a hydroxyalkyl (meth)acrylate.

In a further embodiment of the process according to the invention, in and/or after step b) the hydroxyalkyl (meth) acrylate is selected from the group 2-hydroxyethyl (meth) acrylate, 2-hydroxypropyl (meth)acrylate, 4-hydroxybutyl (meth)acrylate and/or 3-hydroxy-2,2-dimethylpropyl (meth) acrylate.

The present invention relates further to a coating composition comprising a UV absorber-comprising urethane acrylate according to the invention and/or a UV absorber-comprising urethane acrylate obtainable by a process according to the invention.

In one embodiment of the coating composition according to the invention it comprises:
i) UV absorber-comprising urethane acrylate according to the present invention and/or a UV absorber-comprising urethane acrylate obtainable by a process according to the present invention in an amount of from 0.1 to 50 parts by weight (preferably from 4 to 8 wt. %, based on the total amount of the coating composition),
ii) from 12 to 70 parts by weight of at least one $C_2$-$C_{12}$-diol diacrylate or $C_2$-$C_{12}$-diol dimethacrylate, wherein $C_2$-$C_2$ represents a linear alkylene radical which can be optionally substituted by a methyl group or can be interrupted by one or more oxygen atom(s) and optionally substituted by one or more methyl group(s),
iii) from 12 to 40 parts by weight of at least one alkoxylated, preferably ethoxylated, mono-, di-, tri-, tetra-, penta- or hexa-acrylate or alkoxylated, preferably ethoxylated, mono-, di-, tri-, tetra-, penta- or hexa-methacrylate,
iv) from 0 to 40 parts by weight of at least one monomer selected from the group comprising pentaerythritol triacrylate, pentaerythritol tetraacrylate, dipentaerythritol tetraacrylate, dipentaerythritol pentaacrylate, dipentaerythritol hexaacrylate, pentaerythritol trimethacrylate, pentaerythritol tetramethacrylate, dipentaerythritol tetramethacrylate, dipentaerythritol pentamethacrylate, dipentaerythritol hexamethacrylate and possible reaction products thereof with aliphatic or aromatic diisocyanates,
v) from 5 to 60 parts by weight of at least one further mono-, di- or tri-acrylate or mono-, di- or tri-methacrylate,
wherein the sum of the parts by weight of components i) to v) is ≤100 parts by weight, and the coating composition additionally comprises at least
vi) from 0.1 to 10 parts by weight of at least one photoinitiator.

Component ii) is preferably at least one C4-C12-diol diacrylate or C4-C12-diol dimethacrylate, particularly preferably at least one C4-C8-diol diacrylate or C4-C8-diol dimethacrylate. The C2-C12, preferably C4-C12, particularly preferably C4-C8, units are preferably linear alkylene radicals which can be optionally substituted by a methyl group or can be interrupted by one or more oxygen atom(s) and optionally substituted by one or more methyl group(s). They are preferably linear alkene radicals which can optionally be interrupted by one or more oxygen atom(s).

Suitable diol diacrylates or diol dimethacrylates are most particularly preferably those of the general formula (VI)

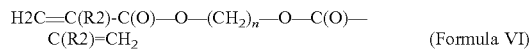

wherein
R2 represents 1-1 or $CH_3$, preferably
n represents an integer from 2 to 12, preferably from 4 to 12, particularly preferably from 4 to 8.

Further suitable diol diacrylates or diol dimethacrylates are most particularly preferably those of the general formula (VII)

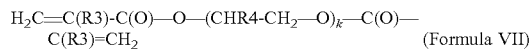

wherein
R3 represents H or CH3, preferably H,
R4 represents H or CH3, and
k represents an integer from 2 to 5, preferably from 2 to 4, Suitable C4-C8-diol diacrylates or -diol dimethacrylates are, for example, diethylene glycol diacrylate, diethylene glycol dimethacrylate, triethylene glycol diacrylate, triethylene glycol dimethacrylate, tetraethylene glycol diacrylate, tetraethylene glycol dimethacrylate, dipropylene glycol diacrylate, dipropylene glycol dimethacrylate, tripropylene glycol diacrylate, tripropylene glycol dimethacrylate, 1,4-butanediol diacrylate, 1,4-butanediol dimethacrylate, 1,5-pentanediol diacrylate, 1,5-pentanediol dimethacrylate, 1,6-hexanediol diacrylate, 1,6-hexanediol dimethacrylate, 3-methyl-1,5-pentanediol diacrylate, 3-methyl-1,5-pentanediol dimethacrylate, 1,7-heptanediol diacrylate, 1,7-heptanediol dimethacrylate, 1,8-octanediol diacrylate and/or 1,8-octanediol dimethacrylate. C4-C12-Diol diacrylates or -diol dimethacrylates which are additionally suitable are, for example, 1,9-nonanediol diacrylate, 1,9-nonanediol dimethacrylate, 2-methyl-1,8-octanediol diacrylate, 2-methyl-1,8- octanediol dimethacrylate, 1,10-decanediol diacrylate, 1,10-decanediol dimethacrylate, 1,11-undecanediol diacrylate, 1,11-undecanediol dimethacrylate, 1,12-dodecanediol diacrylate and/or 1,12-dodecanediol dimethacrylate. C2-C12-Diol diacrylates or -diol dimethacrylates which are additionally suitable are, for example, ethylene glycol diacrylate, ethylene glycol dimethacrylate, 1,3-propanediol diacrylate and/or 1,3-propanediol dimethacrylate. Most particular preference is given to the diacrylates in each case. Particular preference is given to 1,6-hexanediol diacrylate and/or 1,6-hexanediol dimethacrylate, diethylene glycol diacrylate, diethylene glycol dimethacrylate, particularly preferably 1,6-hexanediol diacrylate, diethylene glycol diacrylate.

The coating composition comprises preferably from 12 to 35 parts by weight, particularly preferably from 15 to 30 parts by weight, most particularly preferably from 20 to 30 parts by weight, of component iii). The mentioned parts by weight are the sum of the parts by weight of all the alkoxylated mono-, di- or tri-acrylates or -methacrylates of which component iii) is composed.

The alkoxylated monoacrylates or monomethacrylates for component (iii) can be alkoxylated optionally substituted aliphatic, cycloaliphatic, aromatic, mixed aromatic-aliphatic monoacrylates or monomethacrylates. There are suitable both alkoxylated linear and branched aliphatic monoacrylates or monomethacrylates, in which the alkyl chain can additionally be interrupted by one or more heteroatoms, such as, for example, oxygen atoms. In the case of cycloaliphatic or aromatic monoacrylates or monomethacrylates, heterocyclic or heteroaromatic monoacrylates or monomethacrylates are also suitable.

Examples of such alkoxylated monoacrylates or monomethacrylates are alkoxylated, preferably ethoxylated, methyl acrylate, ethyl acrylate, n-butyl acrylate, isobutyl acrylate, tert-butyl acrylate, 2-ethylhexyl acrylate, isodecyl acrylate, n-lauryl acrylate, C12-C15-alkyl acrylates, n-stearyl acrylate, n-butoxyethyl acrylate, butoxy diethylene glycol acrylate, methoxy triethylene glycol acrylate, cyclohexyl acrylate, tetrahydrofurfuryl acrylate, benzyl acrylate, 2-phenoxyethyl acrylate, isobornyl acrylate, 2-hydroxyethyl acrylate, 2-hydroxypropyl acrylate, 2-hydroxyethyl acrylate, 2-hydroxybutyl acrylate, 2-hydroxybutyl acrylate and the corresponding alkoxylated, preferably ethoxylated, methacrylates.

The alkoxylated diacrylates or dimethacrylates for component (iii) can be, for example, those which are different from the diol diacrylates and dimethacrylates of component ii).

Examples of such alkoxylated diacrylates or dimethacrylates are alkoxylated, preferably ethoxylated, methanediol diacrylate, methanediol dimethacrylate, glycerol diacrylate, glycerol dimethacrylate, neopentyl glycol diacrylate, neopentyl glycol dimethacrylate, 2-butyl-2-ethyl-1,3-propanediol diacrylate, 2-butyl-2-ethyl-1,3-propanediol dimethacrylate, trimethylolpropane diacrylate or trimethylolpropane dimethacrylate.

Examples of alkoxylated triacrylates or trimethacrylates for component (iii) are alkoxylated, preferably ethoxylated, pentaerythritol triacrylate, pentaerythritol trimethacrylate, glycerol triacrylate, glycerol trimethacrylate, 1,2,4-butanetriol triacrylate, 1,2,4-butanetriol trimethacrylate, trimethylolpropane triacrylate, trimethylolpropane trimethacrylate, tricyclodecanedimethanol diacrylate, tricyclodecanedimethanol dimethacrylate, ditrimethylolpropane tetraacrylate or ditrimethylolpropane tetramethacrylate.

Examples of alkoxylated tetra-, penta- or hexa-acrylates are alkoxylated, preferably ethoxylated, pentaerythritol tetraacrylate, dipentaerythritol tetraacrylate, dipentaerythritol pentaacrylate, dipentaerythritol hexaacrylate, pentaerythritol tetramethacrylate, dipentaerythritol tetramethacrylate, dipentaerythritol pentamethacrylate or dipentaerythritol hexamethacrylate.

In the alkoxylated diacrylates or dimethacrylates, triacrylates or trimethacrylates, tetraacrylates or tetramethacrylates, pentaacrylates or pentamethacrylates and/or alkoxylated hexaacrylates or hexamethacrylates of component iii), all the acrylate groups or methacrylate groups or only some of the acrylate groups or methacrylate groups in the monomer in question can be bonded via alkylene oxide groups to the corresponding radical. Arbitrary mixtures of such wholly or partially alkoxylated di-, tri-, tetra-, penta- or hexa-acrylates and -methacrylates can also be used. It is also possible for the acrylate or methacrylate group(s) to be bonded to the aliphatic, cycloaliphatic or aromatic radical of the monomer via a plurality of successive alkylene oxide groups, preferably ethylene oxide groups. The mean number of alkylene oxide or ethylene oxide groups in the monomer is given by the degree of alkoxylation or degree of ethoxylation. The degree of alkoxylation or degree of ethoxylation can preferably be from 2 to 25, particular preference being given to degrees of alkoxylation or degrees of ethoxylation of from 2 to 15, most particularly preferably from 3 to 9.

Component (iii) preferably comprises alkoxylated, preferably ethoxylated, di- and/or tri-acrylates. Component (iii) particularly preferably comprises at least one alkoxylated, preferably ethoxylated, di- or tri-acrylate or at least one alkoxylated, preferably ethoxylated, di- or tri-methacrylate, most particularly preferably an ethoxylated di- or tri-acrylate. In preferred embodiments of the invention, component (iii) comprises at least one ethoxylated triacrylate or trimethacrylate, preferably ethoxylated triacrylate. Particularly preferably, component (iii) comprises alkoxylated trimethylolpropane triacrylate and/or trimethylolpropane trimethacrylate. In preferred embodiments, component (iii) comprises ethoxylated trimethylolpropane triacrylate and/or trimethylolpropane trimethacrylate, preferably ethoxylated trimethylolpropane triacrylate. In preferred embodiments, the degree of ethoxylation of the trimethylolpropane triacrylates and/or trimethylolpropane trimethacrylates is from 2 to 25, particularly preferably from 2 to 15, most particularly preferably from 3 to 9.

The coating composition comprises preferably from 0 to 30 parts by weight, particularly preferably from 0.1 to 30 parts by weight, of component iv). In particularly preferred embodiments, component III) is present in the coating composition. The mentioned parts by weight are the sum of the parts by weight of all the monomers from the mentioned group of which component iv) is composed.

Component iv) is monomers selected from the group comprising pentaerythritol triacrylate, pentaerythritol tetraacrylate, dipentaerythritol tetraacrylate, dipentaerythritol pentaacrylate, pentaerythritol trimethacrylate, pentaerythritol tetramethacrylate, dipentaerythritol tetramethacrylate, dipentaerythritol pentamethacrylate and reaction products thereof with aliphatic or aromatic diisocyanates, as well as comprising dipentaerythritol hexaacrylate and dipentaerythritol hexamethacrylate. Component iv) is preferably mixtures comprising two or more of the monomers mentioned above.

Suitable aliphatic diisocyanates are linear aliphatic, branched aliphatic and/or cycloaliphatic diisocyanates. Examples of such aliphatic diisocyanates are 1,4-butylene diisocyanate, 1,6-hexamethylene diisocyanate (HDI), isophorone diisocyanate (IPDI), 2,2,4- and/or 2,4,4-trimethylhexamethylene diisocyanate, the isomeric bis-(4,4'-isocyanatocyclohexyl)methanes or mixtures thereof of any desired isomer content, 1,4-cyclohexylene diisocyanate, 4-isocyanatomethyl-1,8-octane diisocyanate (nonane triisocyanate), alkyl-2,6-diisocyanatohexanoates (lysine diisocyanates) having alkyl groups having from 1 to 8 carbon atoms, as well as mixtures thereof.

Examples of aromatic diisocyanates are 1,4-phenylene diisocyanate, 2,4- and/or 2,6-toluene diisocyanate (TDI), 1,5-naphthylene diisocyanate, 2,2'- and/or 2,4'- and/or 4,4'-diphenylmethane diisocyanate, 1,3- and/or 1,4-bis-(2-isocyanato-prop-2-yl)-benzene (TMXDI), 1,3-bis(isocyanatomethyl)benzene (XDI), as well as mixtures thereof.

Preferred aliphatic or aromatic diisocyanates are 1,6-hexamethylene diisocyanate (HDI), isophorone diisocyanate (IPDI) or 2,4- and/or 2,6-toluene diisocyanate (TDI).

In embodiments that are most preferred, component iv) comprises pentaerythritol triacrylate, pentaerythritol tetraacrylate, dipentaerythritol tetraacrylate, dipentaerythritol pentaacrylate and/or dipentaerythritol hexaacrylate.

The coating composition comprises preferably from 10 to 60 parts by weight, particularly preferably from 15 to 55 parts by weight, of component v). The mentioned parts by weight are the sum of the parts by weight of all the mono-, di- or tri-acrylates or -methacrylates of which component v) is composed.

The monoacrylates or monomethacrylates for component (IV) can be optionally substituted aliphatic, cycloaliphatic, aromatic, mixed aromatic-aliphatic monoacrylates or monomethacrylates. There are suitable both linear and branched aliphatic monoacrylates or monomethacrylates, in which the alkyl chain can additionally be interrupted by one or more heteroatoms, such as, for example, oxygen atoms.

In the case of cycloaliphatic or aromatic monoacrylates or monomethacrylates, heterocyclic or heteroaromatic monoacrylates or monomethacrylates are also suitable. The monoacrylates or monomethacrylates which are suitable for component (IV) are not alkoxylated.

Examples of such monoacrylates or monomethacrylates are methyl acrylate, ethyl acrylate, n-butyl acrylate, isobutyl acrylate, tert-butyl acrylate, 2-ethyl-hexyl acrylate, isodecyl acrylate, n-lauryl acrylate, C12-C15-alkyl acrylates, n-stearyl acrylate, n-butoxyethyl acrylate, butoxy diethylene glycol acrylate, methoxy triethylene glycol acrylate, cyclohexyl acrylate, tetrahydrofurfuryl acrylate, benzyl acrylate, 2-phenoxyethyl acrylate, isobornyl acrylate, 2-hydroxyethyl acrylate, 2-hydroxypropyl acrylate, 2-hydroxyethyl acrylate, 2-hydroxybutyl acrylate, 2-hydroxybutyl acrylate and the corresponding methacrylates.

The diacrylates or dimethacrylates for component (v) can be, for example, those which are different from the diol diacrylates and dimethacrylates of component ii) and are not alkoxylated.

Examples of such diacrylates or dimethacrylates are methanediol diacrylate, methanediol dimethacrylate, glycerol diacrylate, glycerol dimethacrylate, neopentyl glycol diacrylate, neopentyl glycol dimethacrylate, 2-butyl-2-ethyl-1,3-propandiol diacrylate, 2-butyl-2-ethyl-1,3-propanediol dimethacrylate, trimethylolpropane diacrylate or trimethylolpropane dimethacrylate.

The triacrylates or trimethacrylates for component (v) can be, for example, those which are different from the triacrylates and trimethacrylates of component iv) and are not alkoxylated.

Examples of such triacrylates or trimethacrylates are glycerol triacrylate, glycerol trimethacrylate, 1,2,4-butanetriol triacrylate, 1,2,4-butanetriol trimethacrylate, trimethylolpropane triacrylate, trimethylolpropane trimethacrylate, tricyclodecanedimethanol diacrylate, tricyclodecanedimethanol dimethacrylate, ditrimethylolpropane tetraacrylate or ditrimethylolpropane tetramethacrylate.

Component (v) preferably comprises at least one di- or tri-acrylate or at least one di- or tri-methacrylate. Component (IV) particularly preferably comprises at least one triacrylate or trimethacrylate. Particularly preferably, component (v) comprises trimethylolpropane triacrylate and/or trimethylolpropane trimethacrylate, preferably trimethylolpropane triacrylate.

Suitable photoinitiators (UV-driven initiators) preferably have a high photochemical reactivity and an absorption band in the near-UV range (>300 nm and particularly preferably >350 nm).

Suitable photoinitiators are preferably those selected from the group of acylphosphine oxide derivatives, α-aminoalkylphenone derivatives, hydroxyalkylphenones, benzophenones, benzil ketals, methylbenzoyl formate and phenylacetophenones.

Examples of such photoinitiators are benzophenone, bis (2,4,6-trimethylbenzoyl)phenylphosphine oxide (Irgacure® 819 from BASF AG), 1-hydroxy-cyclohexyl phenyl ketone (Irgacure® 184 from BASF AG), 2-benzyl-2-(dimethylamino)-1-(4-morpholinophenyl)-1-butanone (Irgacure® 369 from BASF AG), 2-methyl-1-[4-(methylthio)phenyl]-2-morpholino-1-propanone (Irgacure® 907 from BASF AG), (1-hydroxycyclohexyl)phenylmethanone (Irgacure® 1800 from BASF AG), 2-hydroxy-2-methyl-1-phenyl-1-propanone (Irgacure® 1700 from BASF AG), bis(2,6-dimethylbenzoyl)(2,4,4-trimethylpentyl)phosphine oxide, bis(2,6-dimethoxybenzoyl)(2,4,4-trimethylpentyl)phosphine oxide, (2,4,6-trimethylbenzoyl)diphenylphosphine oxide (Lucirin® TPO Solid from BASF AG), 2,4,6-trimethylbenzoylethoxyphenylphosphine oxide (Lucirin® TPO-L from BASF AG), benzoylphosphonic acid bis(2,6-dimethylphenyl) ester (Lucirin® 8728 from BASF AG), and 2-hydroxy-2-methyl-1-phenyl-1-propanone (Darocur® 4265 from BASF AG).

Also suitable are mixtures of those photoinitiators with one another.

The coating composition can additionally comprise, in addition to the 100 parts by weight of components i) to v), optionally one or more coating additives. Such coating additives can be selected, for example, from the group comprising stabilisers, flow agents, surface-active additives, pigments, dyes, inorganic nanoparticles, adhesion promoters, IR absorbers, preferably from the group comprising stabilisers, flow agents, surface-active additives and inorganic nanoparticles. The coating composition preferably comprises, in addition to the amount of photoinitiator and in addition to the 100 parts by weight of components i) to v), from 0 to 20 parts by weight, particularly preferably from 0 to 10 parts by weight, most particularly preferably from 0.1 to 10 parts by weight, of at least one further coating additive as component vii). Preferably, the total amount of all coating additives present in the coating composition is from 0 to 20 parts by weight, particularly preferably from 0 to 10 parts by weight, most particularly preferably from 0.1 to 10 parts by weight.

The coating composition can comprise inorganic nanoparticles for increasing the mechanical resistance, such as, for example, scratch resistance and/or pencil hardness.

Suitable nanoparticles are inorganic oxides, mixed oxides, hydroxides, sulfates, carbonates, carbides, borides and nitrides of elements of main groups II to IV and/or elements of subgroups I to VIII of the periodic system including the lanthanides. Preferred nanoparticles are silicon oxide, aluminium oxide, cerium oxide, zirconium oxide, niobium oxide, zinc oxide or titanium oxide nanoparticles; silicon oxide nanoparticles are particularly preferred.

The particles used preferably have mean particle sizes (measured by means of dynamic light scattering in dispersion determined as the Z-average) smaller than 200 nm, preferably from 5 to 100 nm, particularly preferably from 5 to 50 nm. Preferably at least 75%, particularly preferably at least 90%, most particularly preferably at least 95%, of all the nanoparticles used have the sizes defined above.

The coating composition can additionally comprise, in addition to the 100 parts by weight of components i) to v), optionally one or more organic solvents. Such organic solvents can be selected, for example, from the group comprising aromatic solvents, such as, for example, xylene or toluene, ketones, such as, for example, acetone, 2-butanone, methyl isobutyl ketone, diacetone alcohol, alcohols, such as, for example, methanol, ethanol, isopropanol, butanol, 2-methoxy-propyl alcohol, ethers, such as, for example, 1,4-dioxane, ethylene glycol n-propyl ether, or esters, such as, for example, ethyl acetate, butyl acetate, 1-methoxy-2-propyl acetate, or mixtures comprising those solvents. Particular preference is given to ethanol, isopropanol, butanol, ethyl acetate, butyl acetate, 2-methoxy-propyl alcohol, diacetone alcohol, xylene or toluene. Most particular preference is given to isopropanol, butanol, ethyl acetate, butyl acetate, 2-methoxy-propyl alcohol. The coating composition preferably comprises, in addition to the amount of photoinitiator and in addition to the 100 parts by weight of components i) to v), from 0 to 300 parts by weight, particularly preferably from 0 to 200 parts by weight, most particularly preferably from 10 to 150 parts by weight, of at least one organic solvent as component viii). Preferably, the total amount of all the organic solvents present in the coating composition is from 0 to 300 parts by weight, particularly preferably from 0 to 200 parts by weight, most particularly preferably from 10 to 150 parts by weight.

The coating compositions can be prepared in a simple manner either by combining the individual components i) to vi) and, where appropriate, the optional components vii) and viii) in the absence of solvent(s) and mixing them together by stirring or, in the presence of solvent(s), by introducing them into the solvent or solvents, for example, and mixing them together by stirring. Preferably, the photoinitiator is first dissolved in the solvent or solvents or, for example, in component I) and then the further components are added. Optionally, purification by means of filtration, preferably by means of fine filtration, is then carried out.

The liquid form of the UV absorber (formula I, I-1, I-2) makes the admixture of components i) to vi) particularly simple, and the adapted structure of the absorber makes the resulting finished coating stable and transparent in all steps of the coating process and as a result particularly suitable for the production of the UV-protecting, weather-resistant, clear and hard surface of a plastics part or of a film (particularly of polycarbonate).

The present invention further provides a method for coating a substrate, comprising the steps:
applying a coating composition according to the invention to a substrate,
curing the previously applied coating composition by irradiation with UV light.

Preferably, in the first step, the composition is applied to the surface of the substrate by flood coating, dipping, spraying, roller coating or spin coating and is then flashed off at room temperature and/or elevated temperature (preferably at from 20 to 200° C., particularly preferably at from 40 to 120° C.). The surface of the second layer can be pretreated by cleaning or activation.

Preferably, in the second step (ii), curing of the first layer takes place by means of UV light, there being used as the UV light source preferably a mercury vapour lamp, doped with iron, or a pure mercury vapour lamp, or one doped with gallium. Irradiation is thus carried out with light having a wavelength of 254 nm.

By means of the dose according to the invention of at least 3 $J/cm^2$, curing of the entire layer of the coating composition and incorporation of the UV absorber into the polymer matrix that forms are achieved.

In one embodiment of the method according to the invention, the substrate is a thermoplastic substrate.

In a further embodiment of the method according to the invention, the substrate is a polycarbonate substrate.

Substrates

Thermoplastic polymers of the substrate within the meaning according to the invention are polycarbonate, polyester carbonate, polyesters (such as, for example, polyalkylene terephthalate), polymethyl methacrylate, polyphenylene ether, graft copolymers (such as, for example, ABS) and mixtures thereof.

The second layer is preferably polycarbonate, in particular homopolycarbonate, copolycarbonate and/or thermoplastic polyester carbonate.

They preferably have mean molecular weights $M_w$ of from 18,000 to 40,000, preferably from 22,000 to 36,000 and in particular from 24,000 to 33,000, determined by measuring the relative solution viscosity in dichloromethane or in mixtures of equal amounts by weight of phenol/o-dichlorobenzene calibrated by light scattering.

To the polycarbonates according to the invention and the optionally further present-stabilisers, heat stabilisers, antistatics and pigments in the conventional amounts are added; the demoulding behaviour and/or the flow behaviour can optionally also be improved by the addition of external demoulding agents and/or flow agents (e.g. alkyl and aryl phosphites, phosphates, phosphanes, low molecular weight carboxylic acid esters, halogen compounds, salts, chalk, quartz flour, glass and carbon fibres, pigments and combinations thereof). Such compounds are described, for example, in WO 99/55772, p. 15-25, EP 1 308 084 and in the corresponding chapters of "Plastics Additives Handbook", ed. Hans Zweifel, $5^{th}$ Edition 2000, Hanser Publishers, Munich.

For the preparation of polycarbonates, reference is made by way of example to WO 2004/063249 A1, WO 2001/05866 A1, WO 2000/105867, U.S. Pat. No. 5,340,905, U.S. Pat. No. 5,097,002, U.S. Pat. No. 5,717,057 and the literature cited therein.

The preparation of polycarbonates is preferably carried out by the interfacial process or the melt transesterification process and is described in the following using the interfacial process by way of example.

Compounds which are preferably to be used as starting compounds are bisphenols of the general formula HO—R—OH, wherein R is a divalent organic radical having from 6 to 30 carbon atoms which contains one or more aromatic groups.

Examples of such compounds are bisphenols which belong to the group of the dihydroxydiphenyls, bis(hydroxyphenyl)alkanes, indane bisphenols, bis(hydroxyphenyl) ethers, bis(hydroxyphenyl)-sulfones, bis(hydroxyphenyl) ketones and α,α-bis(hydroxyphenyl)-diisopropylbenzenes.

Particularly preferred bisphenols which belong to the above-mentioned groups of compounds are bisphenol A, tetraalkylbisphenol A, 4,4-(meta-phenylenediisopropyl)diphenol (bisphenol M), 4,4-(para-phenylenediisopropyl)diphenol, 1,1-bis-(4-hydroxyphenyl)-3,3,5-trimethylcyclohexane (BP-TMC) and optionally mixtures thereof.

The bisphenol compounds to be used according to the invention are optionally reacted with carbonic acid compounds, in particular phosgene, or, in the case of the transesterification process, with diphenyl carbonate or dimethyl carbonate.

Polyester carbonates are preferably obtained by reacting the bisphenols already mentioned, at least one aromatic dicarboxylic acid and optionally carbonic acid equivalents. Suitable aromatic dicarboxylic acids are, for example, phthalic acid, terephthalic acid, isophthalic acid, 3,3'- or 4,4'-diphenyldicarboxylic acid and benzophenonedicarboxylic acids. Some, up to 80 mol %, preferably from 20 to 50 mol %, of the carbonate groups in the polycarbonates can be replaced by aromatic dicarboxylic acid ester groups.

Inert organic solvents used in the interfacial process are, for example, dichloromethane, the various dichloroethanes and choropropane compounds, tetrachloromethane, trichloromethane, chlorobenzene and chlorotoluene; chlorobenzene or dichloromethane or mixtures of dichloromethane and chlorobenzene are preferably used.

The interfacial reaction can be accelerated by catalysts such as tertiary amines, in particular N-alkylpiperidines or onium salts. Tributylamine, triethylamine and N-ethylpiperidine are preferably used. In the case of the melt transesterification process, the catalysts mentioned in DE-A 4 238 123 are preferably used.

The polycarbonates can be branched in a deliberate and controlled manner by the use of small amounts of branching agents. Some suitable branching agents are: phloroglucinol, 4,6-dimethyl-2,4,6-tri-(4-hydroxyphenyl)-heptene-2; 4,6-dimethyl-2,4,6-tri-(4-hydroxyphenyl)-heptane; 1,3,5-tri-(4-hydroxy-phenyl)-benzene; 1,1,1-tri-(4-hydroxyphenyl)-ethane; tri-(4-hydroxyphenyl)-phenylmethane; 2,2-bis-[4,4-bis-(4-hydroxyphenyl)cyclohexyl]-propane; 2,4-bis-(4-hydroxyphenyl-isopropyl)-phenol; 2,6-bis-(2-hydroxy-5'-methyl-benzyl)-4-methylphenol; 2-(4-hydroxyphenyl)-2-(2,4-dihydroxyphenyl)-propane; hexa-(4-(4-hydroxyphenyl-isopropyl)-phenyl)-orthoterephthalic acid ester; tetra-(4-hydroxy-phenyl)-methane; tetra-(4-(4-hydroxyphenyl-isopropyl)-phenoxy)-methane; α,α',α''-tris-(4-hydroxy-phenyl)-1,3,5-triisopropylbenzene; 2,4-dihydroxybenzoic acid; trimesic acid; cyanuric chloride; 3,3-bis-(3-methyl-4-hydroxyphenyl)-2-oxo-2,3-dihydroindole; 1,4-bis-(4',4''-dihydroxytriphenyl)-methyl)-benzene and in particular: 1,1,1-tri-(4-hydroxyphenyl)-ethane and bis-(3-methyl-4-hydroxyphenyl)-2-oxo-2,3-dihydroindole.

The from 0.05 to 2 mol %, based on diphenols used, of branching agents or mixtures of branching agents which are optionally to be used concomitantly can be used together with the diphenols or alternatively can be added to the synthesis at a later stage.

As chain terminators there are preferably used phenols such as phenol, alkylphenols such as cresol and 4-tert-butylphenol, chlorophenol, bromophenol, cumylphenol or mixtures thereof in amounts of from 1 to 20 mol %, preferably from 2 to 10 mol %, per mol of bisphenol. Preference is given to phenol, 4-tert-butylphenol and cumylphenol.

Chain terminators and branching agents can be added to the syntheses separately or together with the bisphenol.

The preparation of polycarbonates by the melt transesterification process is described by way of example in DE-A 4 238 123.

Polycarbonates which are preferred according to the invention for the second layer of the multilayer product according to the invention are the homopolycarbonate based on bisphenol A, the homopolycarbonate based on 1,1-bis-(4-hydroxyphenyl)-3,3,5-trimethylcyclohexane, and the copolycarbonates based on the two monomers bisphenol A and 1,1-bis-(4-hydroxyphenyl)-3,3,5-trimethylcyclohexane.

The homopolycarbonate based on bisphenol A is particularly e ed.

The polycarbonate can comprise stabilisers. Suitable stabilisers are, for example, phosphines, phosphites or Si-comprising stabilisers and further compounds described in EP-A 0 500 496. Examples which may be mentioned are triphenyl phosphites, diphenylallyl phosphites, phenyldialkyl phosphites, tris-(nonylphenyl) phosphite, tetrakis-(2, 4-di-tert-butylphenyl)-4,4'-biphenylene diphosphonite and triaryl phosphite. Triphenylphosphine and tris-(2,4-di-tert-butylphenyl) phosphite are particularly preferred.

The polycarbonate-comprising substrate of the multilayer product according to the invention can further comprise from 0.01 to 0.5 wt. % of the esters or partial esters of mono- to hexa-hydric alcohols, in particular of glycerol, pentaerythritol or Guerbet alcohols.

Monohydric alcohols are, for example, stearyl alcohol, palmityl alcohol and Guerbet alcohols.

A dihydric alcohol is, for example, glycol.

A trihydric alcohol is, for example, glycerol.

Tetrahydric alcohols are, for example, pentaerythritol and mesoerythritol.

Pentahydric alcohols are, for example, arabitol, ribitol and xylitol.

Hexahydric alcohols are, for example, mannitol, glucitol (sorbitol) and dulcitol.

The esters are preferably the monoesters, diesters, triesters, tetraesters, pentaesters and hexaesters or mixtures thereof, in particular random mixtures, of saturated, aliphatic $C_{10}$- to $C_{36}$-monocarboxylic acids and optionally hydroxy-monocarboxylic acids, preferably with saturated, aliphatic $C_{14}$- to $C_{32}$-monocarboxylic acids and optionally hydroxy-monocarboxylic acids.

The commercially available fatty acid esters, in particular of pentaerythritol and of glycerol, can comprise <60% of different partial esters as a result of their production.

Saturated, aliphatic monocarboxylic acids having from 10 to 36 carbon atoms are, for example, capric acid, lauric acid, myristic acid, palmitic acid, stearic acid, hydroxystearic acid, arachidic acid, behenic acid, lignoceric acid, cerotinic acid and montanic acids.

Preferred saturated, aliphatic monocarboxylic acids having from 14 to 22 carbon atoms are, for example, myristic acid, palmitic acid, stearic acid, hydroxystearic acid, arachidic acid and behenic acid.

Saturated, aliphatic monocarboxylic acids such as palmitic acid, stearic acid and hydroxystearic acid are particularly preferred.

The saturated, aliphatic $C_{10}$- to $C_{36}$-carboxylic acids and the fatty acid esters are, as such, either known from the literature or can be prepared by processes known from the literature. Examples of pentaerythritol fatty acid esters are those of the particularly preferred monocarboxylic acids mentioned above. Esters of pentaerythritol and of glycerol with stearic acid and palmitic acid are particularly preferred.

Esters of Guerbet alcohols and of glycerol with stearic acid and palmitic acid and optionally hydroxystearic acid are also particularly preferred.

The invention also includes a multilayer structure comprising the substrate A and a protective layer B produced by curing the composition according to the invention. Further layers are optionally possible, either on the cured composition or on the substrate before the composition according to the invention is applied. Further layers with a layer sequence B-A-B are likewise possible. The layers B can be identical or different according to the described composition.

The multilayer products according to the invention, or the thermoplastic polymers used for the production, can comprise organic dyes, inorganic dyeing pigments, fluorescent dyes and, particularly preferably, optical brighteners.

The present invention relates further to a coated substrate obtainable by a method according to the invention.

EXAMPLES

The invention will be described further by means of the following examples, but without being limited thereto.

Example 1

400 g of Tinuvin® 479 (BASF), 945 g of 2-butyl-2-ethyl-1,3-propanediol (Aldrich) and 29 g of dibutyltin oxide (Aldrich) were weighed, combined and stirred for 5 hours at 155° C. The octanol that formed was then distilled off under a vacuum of from 10 to 20 mbar. The mixture was cooled and stirred into 2500 ml of methanol. The precipitate was filtered off and dried in vacuo. The solid was dissolved in 700 ml of a mixture of toluene/ethyl acetate (8:1). The solution was filtered through a layer (10 cm thick) of silica gel. The filtrate was concentrated by evaporation. The solid was suspended in methanol, brought onto the filter and then dried at 40° C. in vacuo. This product is also referred to in the following examples as the "intermediate" of formula (IV-4).

Yield 366 g (88% of theory)
Melting point 80.2° C.
Elemental analysis: $C_{45}H_{45}N_3O_5$ (707.88)
Calc.: C76.36; 116.41; N5.94.
Found: C76.00; H6.40; N5.90.

Example 2

Analogously to Example 1 there were prepared from 153 g of Tinuvin® 479 and 300 g of 2,2-diethyl-1,3-propanediol 125 g (80% of theory) of the intermediate of formula (IV-3).

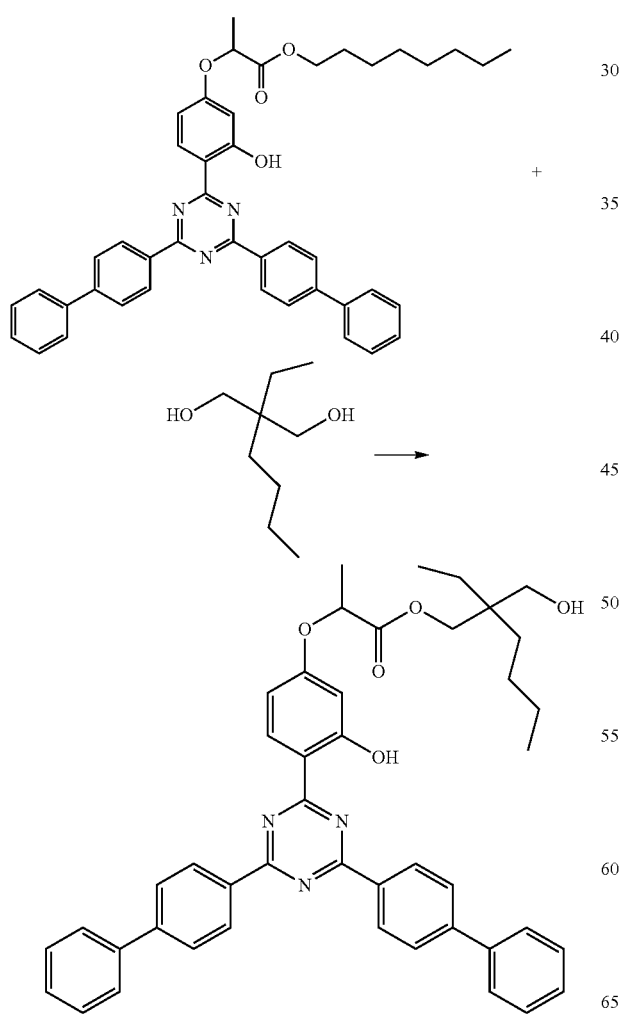

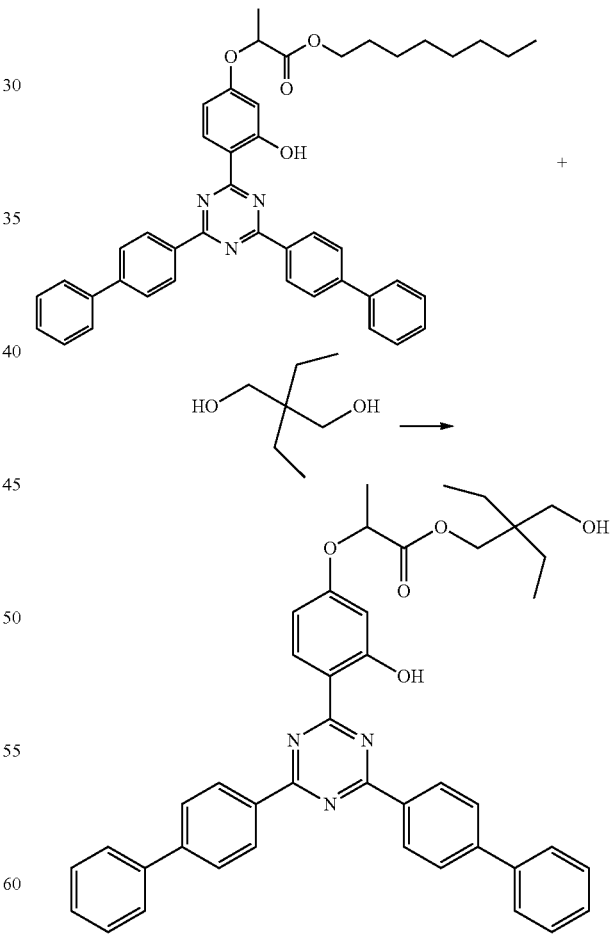

Melting point 107° C.
Elemental analysis: $C_{43}H_{41}N_3O_5$ (679.82)
Calc.: C75.97; 1-16.08; N6.18.
Found: C75.60; 1-16.20; N6.20.

Example 3

Analogously to Example 1 there were prepared from 400 g of Tinuvin® 479 and 532 g of 2-methyl-1,3-propanediol 294 g (78% of theory) of the intermediate of formula (IV-1).

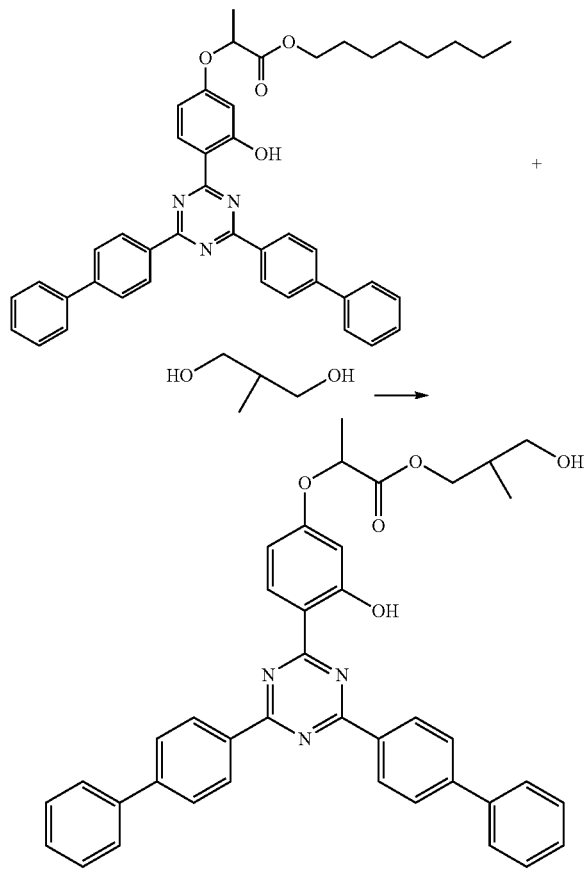

Melting point 153° C.
Elemental analysis: $C_{40}H_{35}N_3O_5$ (637.74)
Calc.: C75.34; H5.53; N6.59.
Found: C75.30; 1-15.70; N6.50.

Example 4

Analogously to Example 1 there were prepared from 899.9 g of Tinuvin® 479 and 1382.6 g of 2,2-dimethyl-1,3-propanediol 722.7 g (83.5% of theory) of the intermediate of formula (IV-2).

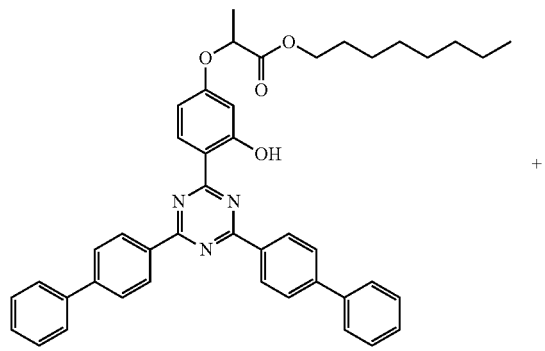

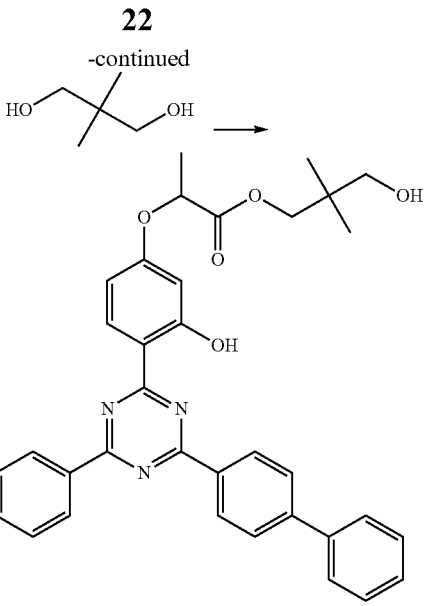

Melting point 173° C.

Example 5

Desmolux® D100 (Bayer MaterialScience) is an isocyanate group-comprising urethane acrylate, free of reactive diluent, with a viscosity (23° C.) of 10,000±2500 mPas and an NCO content of 12.8±1%.

6.8 g of the intermediate obtained from Example 2 were dissolved in 11.61 g of 2-hydroxyethyl acrylate at 100° C. The solution was cooled to 65° C. and added, with stirring, to the Desmolux® D1.00 (66 g) preheated to 65° C. The reaction mixture was stirred for a further 5 hours at 65° C. A further 10.5 g of 2-hydroxyethyl acrylate were added to the reaction mixture, and it was allowed to react for 2 hours. Heating was discontinued. 40.65 g of isopropanol were added and stirred in. A clear light-yellow liquid of medium viscosity formed. The residual NCO content was <0.1%, the solids content was 70 wt. %. The effective UV absorber content (remainder of the substance from Example 2) in the resin was 7.5 wt % (solid/solid).

Example 6

28.55 g of the intermediate obtained from Example 2 were dissolved in a mixture of 50 g of butyl acetate and 11.61 g of 2-hydroxyethyl acrylate at 100° C. The solution was cooled to 65° C. and added, with stirring, to the Desmolux® D100 (66 g) preheated to 65° C. The reaction mixture was stirred for a further 6 hours at 65° C. A further 6.8 g of 2-hydroxyethyl acrylate were added to the reaction mixture, and it was allowed to react for 2 hours. Butyl acetate was distilled off completely in vacuo (1-2 mbar) and at a bath temperature of 40° C. 48.5 g of isopropanol were added and stirred in at 65° C. A clear yellow liquid of medium viscosity (product of Example 6) with a residual NCO content of <0.1%, a viscosity (23° C.) of 282 mPas and a solids content of 70 wt. % was obtained. The effective UV absorber content (remainder of the substance from Example 2) in the resin was 25 wt % (solid/solid).

Example 7

68 g of the intermediate obtained from Example 2 were dissolved in 150 g of butyl acetate at 100° C. The solution was cooled to 90° C. and added, with stirring, to the Desmolux® D100 (66 g) preheated to 90° C. The reaction mixture was stirred for a further 8 hours at 90° C. and then cooled to 65° C. 11.7 g of 2-hydroxyethyl acrylate were added to the reaction mixture, and it was allowed to react for 2 hours. Butyl acetate was distilled off completely in vacuo (1-2 mbar) and at a bath temperature of from 60 to 80° C. A clear yellow-orange liquid of very high viscosity (solid at room temperature) (product of Example 7) with a residual NCO content of <0.1%, a viscosity (80° C.) of 60,000 mPas and a solids content of 100 wt. % was obtained. The effective UV absorber content (remainder of the substance from Example 2) in the resin was 46 wt. % (solid/solid).

30 g of 1-methoxy-2-propanol are added at 100° C. to 70 g of resin (product of Example 7). A clear yellow viscous liquid with a viscosity (23° C.) of 2110 mPas and a solids content of 70 wt. % is obtained.

Example 8

2101.3 g of the intermediate obtained from Example 4 were dissolved in 3877.6 g of diacetone alcohol at 130° C. The solution was cooled to 80° C., filtered through a T1000 filter (Seitz) and added, with stirring, to the Desmolux® D100 (5280.0 g) preheated to 90° C. The reaction mixture was stirred for a further 4 hours at 90° C. and then cooled to 80° C. The NCO content was determined. The calculated amount of 862.0 g of 2-hydroxyethyl acrylate was then added to the reaction mixture, and it was allowed to react for 8 hours. The mixture was then discontinued, cooled and pressed into waiting vessels through a T5500 filter (Seitz).

Yield: 11,568 g

NCO content of the product: <0.1%; tin content: <1 mg/kg

Analytical gel permeation chromatography: $M_w=2.06*10^3$; $M_n=1.02*10^3$. Amount by weight of molecules with molar mass between 500 and 800 g/mol: 2.4%. This shows that the intermediate obtained from Example 4 has for the most part reacted to completion and is bonded to urethane acrylate. Solids content of the product (after 2 hours at 140° C.): 70.4%; viscosity (23° C.): 8480 mPas.

Example 9

21.5 g of the intermediate obtained from Example 1 in powder form were added in portions, with stirring, to the Desmolux® D100 (66 g) preheated to 95° C. The reaction mixture was stirred for a further 4 hours at 95° C. and then cooled to 80° C. 19.8 g of 2-hydroxyethyl acrylate were added to the reaction mixture, and it was allowed to react for 2 hours. Heating was discontinued. 45.9 g of isopropanol were added to the clear yellow liquid resin and stirred in. A clear light-yellow liquid of medium viscosity formed. Residual NCO content: <0.1%, viscosity (23° C.): 618 mPas, solids content: 70 wt. %. The effective UV absorber content (remainder of the substance from Example 4) in the resin was 20 wt. % (solid/solid).

Example 10

28.55 g of the intermediate obtained from Example 1 in powder form were added in portions, with stirring, to the Desmolux® D100 (66 g) preheated to 95° C. The reaction mixture was stirred for a further 4 hours at 95° C. and then cooled to 80° C. 18.7 g of 2-hydroxyethyl acrylate were added to the reaction mixture, and it was allowed to react for 2 hours. Heating was discontinued. 48.5 g of 1-methoxy-2-propanol were added to the clear yellow liquid resin and stirred in. A clear light-yellow liquid of medium viscosity formed. Residual NCO content: <0.1%, viscosity (23° C.): 1360 mPas, solids content: 70 wt. %. The effective UV absorber content (remainder of the substance from Example 4) in the resin was 25 wt. % (solid on solid).

Example 11

For the production of a scratch-resistant coating, the following coating composition ("Base coat G") was used as the base coat. The amounts by weight of the components were:

1,6-Hexanediol diacrylate (HDDA) 48.8;
Trimethylolpropane triacrylate (TMPTA) 20.7;
Ethoxylated TMPTA 20.7;
Pentaerythritol tetraacrylate (PTTA) 9.8
Total: 100 parts by weight.

For the production of a coating composition according to the invention, the following components were combined:

| | |
|---|---|
| UV absorber (product from Example 9; 70% solid in isopropanol) | 6.00 |
| Base coat G | 22.40 |
| Isopropanol | 26.20 |
| Irgacure 184 (BASF) | 1.20 |
| Darocur 4265 (BASF) | 0.06 |
| Tinuvin 123 (BASF) | 0.14 |

Total: 56 parts by weight. The coating composition had a solids content of 50% and a viscosity (23° C.) of less than 10 mPas.

Example 12

For the production of a coating composition according to the invention, the following components were combined:

| | |
|---|---|
| UV absorber (product from Example 10; 70% solid in 1-methoxy-2-propanol) | 4.80 |
| Base coat G (Example 11) | 23.24 |
| 1-Methoxy-2-propanol | 26.56 |
| Irgacure 184 (BASF) | 1.20 |
| Darocur 4265 (BASF) | 0.06 |
| Tinuvin 123 (BASF) | 0.14 |

Total: 56 parts by weight. The coating composition had a solids content of 50% and a viscosity (23° C.) of less than 10 mPas.

Example 13

Comparative Example

For the production of a comparative coating composition, the following components were combined:

| | |
|---|---|
| Base coat G (Example 11) | 26.60 |
| 1-Methoxy-2-propanol | 28.00 |
| Irgacure 184 (BASF) | 1.20 |
| Darocur 4265 (BASF) | 0.06 |
| Tinuvin 123 (BASF) | 0.14 |

Total: 56 parts by weight. The coating composition had a solids content of 50% and a viscosity (23° C.) of less than 10 mPas.

Example 14

From a polycarbonate (PC) film (Makrofol® DE 1-1 cc, thickness 500 µm) provided with laminating films on both sides, the laminating films were removed from both sides. The films were coated without wet cleaning and without thermal pretreatment.

The liquid coating formulations from Examples 11, 12 and 13 were applied to the films by means of the Zehntner ZAA 2300 film applicator coater (universal coating knife, drawing speed 30 mm/s). The coatings were dried at 60° C. for 10 minutes and cured with a mercury radiator (power 80 W/cm lamp length) with a dose of about 3000 mJ/cm².

The layer thickness of the coatings was measured by observing the cut edge under an optical microscope. Method—incident light, bright field, 500× magnification.

The extinction of the coating according to the invention after application to a polycarbonate film and subsequent curing was determined at 350 nm by means of a Cary 50 UV-Vis spectrophotometer from Varian Inc., USA, an uncoated but otherwise identical polycarbonate film being used as the background spectrum.

The pencil hardness according to ISO 15184, the adhesion according to the cross-cut test (ISO 2409) and the solvent resistance to butanol, methyl ethyl ketone, ethyl acetate and N-ethylpyrrolidone (1 hour; in accordance with EN ISO 2812-3:2007) were determined.

|  | Example 11 | Example 12 | Example 13 |
|---|---|---|---|
| Layer thickness (µm) | 10 | 20 | 10 |
| Optical density (350 nm) | 2.61 | 3.19 | 0.02 |
| Adhesion (cross-cut) | 0 (OK) | 0 (OK) | 0 (OK) |
| Adhesion (after 4 hours in boiling water) | 0 (OK) | 0 (OK) | 0 (OK) |
| Solvent resistance (in above-mentioned solvents, 1 hour) | all 0 (OK) | all 0 (OK) | all 0 (OK) |
| Pencil hardness | HB | HB | HB |

The values show that, by the introduction according to the invention of the UV absorbers, high absorbing power in the UV range can be produced. Nevertheless, the UV absorbers according to the invention do not affect the adhesion, solvent resistance and hardness of the coating at all.

Example 15

In order to test the UV-protecting action of the UV absorber-comprising coating on the substrate, the samples were subjected to an accelerated weathering test SAE J 2412. Exposure time: to a radiation dose of 64,000 kJ/m². The colour change of the sample was measured in L*,a*,b* coordinates and shown as the total colour difference ΔE.

|  | Example 11 | Example 12 | Example 13 |
|---|---|---|---|
| Colour values L*, a*, b* before irradiation | 95.1; −0.7; 2.2 | 95.2; −0.7; 2.2 | 95.0; −0.7; 2.3 |
| Colour values L*, a*, b* after 64,000 kJ/m² | 94.9; −0.8; 2.4 | 95.0; −0.8; 2.4 | 93.9; −2.5; 9.9 |
| Total colour difference ΔE* by weathering | 0.3 | 0.3 | 7.9 |

The values show that the UV absorbers according to the invention, when introduced into a scratch-resistant coating, permit only a minimal change in the colour of the substrate by weathering. Unprotected substrates yellow to a considerable degree.

The invention claimed is:

1. A UV absorber-comprising urethane acrylate of formula (I):

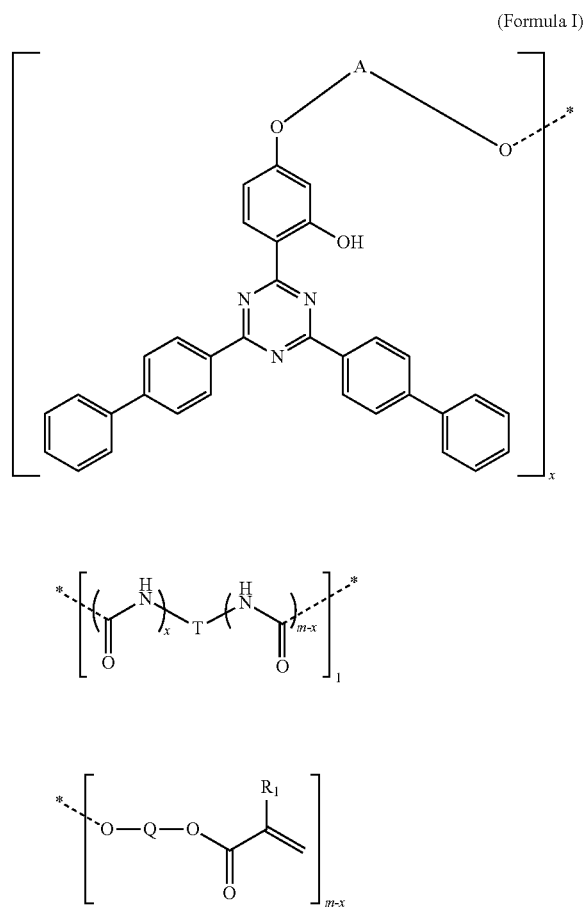

(Formula I)

wherein $R_1$ is a hydrogen or a methyl radical,

Q is a linker of hydroxyalkyl (meth)acrylate selected from the group consisting of 2-hydroxyethyl (meth)acrylate, 2-hydroxypropyl (meth)acrylate, 4-hydroxybutyl (meth)acrylate, and 3-hydroxy-2,2-dimethylpropyl (meth)acrylate, T is a nucleus of an aliphatic or cycloaliphatic polyisocyanates $T(NCO)_m$ which have cyclic isocyanurate, uretdione, iminooxadiazinedione or oxadiazinetrione structures, as well as branched biuret structures in the case of cycloaliphatic polyisocyanates, m corresponds to the original average NCO functionality of the polyisocyanate used and is equal to or greater than 2, A represents an optionally substituted linear or branched linker from carbon, oxygen, nitrogen, sulfur, phosphorus and/or silicon in the chain, and x represents an average molar content of the bonded UV absorber radical and is less than m.

2. The UV absorber-comprising urethane acrylate according to claim 1, wherein the urethane acrylate has the structure according to formula (I-1):

(Formula I-1)

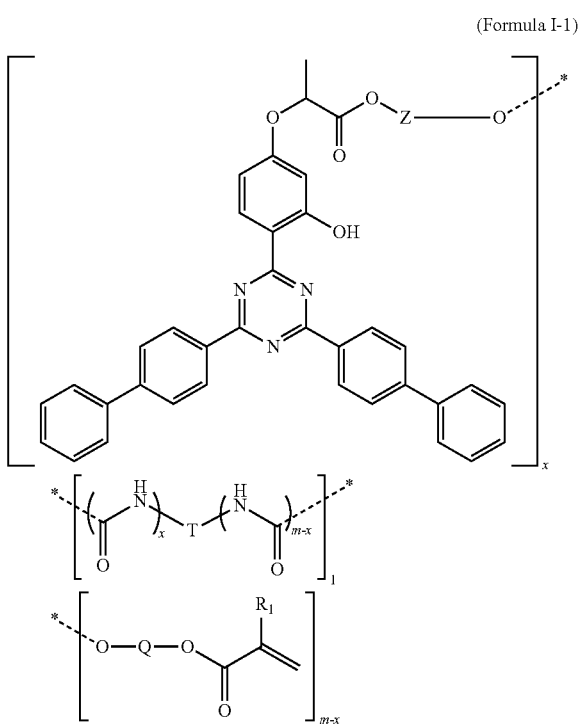

wherein

Z represents an optionally substituted linear or branched $C_{1-20}$-alkylene radical or $C_{1-20}$-alkylene ether radical, and T, Q, m, x and $R_1$ have the meanings given above for the compounds of formula (I).

3. A process for the preparation of a UV absorber-comprising urethane acrylate, comprising the steps:

a) reacting a compound of the formula:

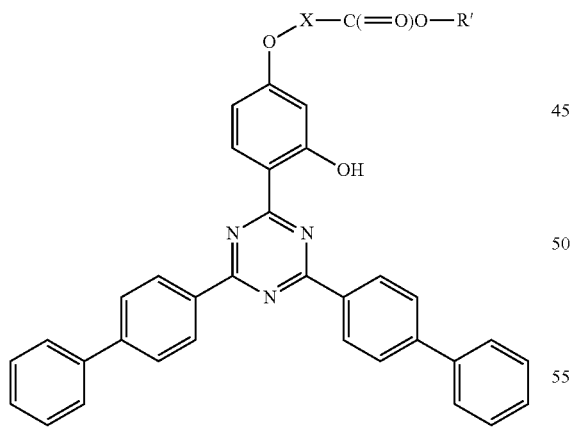

wherein X represents branched or unbranched $C_{1-20}$-alkyl and R' represents branched or unbranched $C_{1-20}$-alkyl, $C_{4-12}$-cycloalkyl, or $C_{6-12}$-aryl optionally substituted by $C_{1-12}$-alkyl, $C_{1-12}$-alkoxy, CN and/or by halogen with an at least difunctional alcohol;

b) reacting the product obtained in step a) with
  bi) an aliphatic or cycloaliphatic, isocyanate group-comprising urethane acrylate which has cyclic isocyanurate, uretdione, iminooxadiazinedione or oxadiazinetrione structures or, in the case of a cycloaliphatic urethane acrylate, can further have branched biuret structures,
  and/or with
  bii) an aliphatic or cycloaliphatic, isocyanate group-comprising polyisocyanate which has cyclic isocyanurate, uretdione, iminooxadiazinedione or oxadiazinetrione structures or, in the case of a cycloaliphatic polyisocyanate, can further have branched biuret structures, wherein the reaction in step b) further takes place in the presence of a hydroxyalkyl (meth)acrylate and/or after the reaction in step b) the resulting product is further reacted with a hydroxyalkyl (meth)acrylate.

4. The process according to claim 3, wherein in step a) in formula X represents $CH(CH_3)$.

5. The process according to claim 3, wherein in step a) in formula R' represents n-octyl or isooctyl.

6. The process according to claim 3, wherein in step a) the at least difunctional alcohol is selected from the group 2-butyl-2-ethyl-1,3-propanediol, 2,2-diethyl-1,3-propanediol, 2-methyl-1,3-propanediol and/or 2,2-dimethyl-1,3-propanediol.

7. The process according to claim 3, wherein the product obtained from step a) is selected from:

(Formula (IV-1))

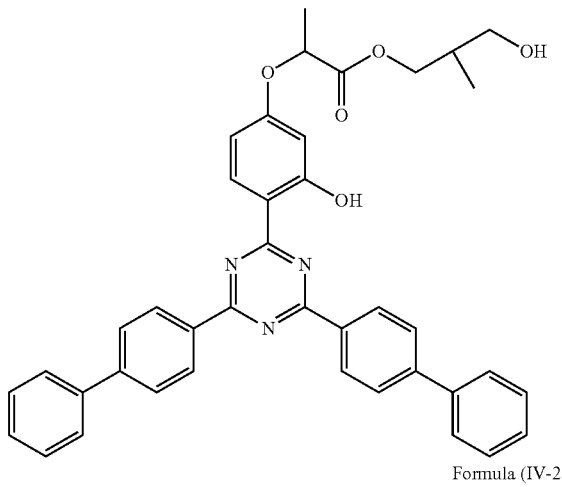

Formula (IV-2)

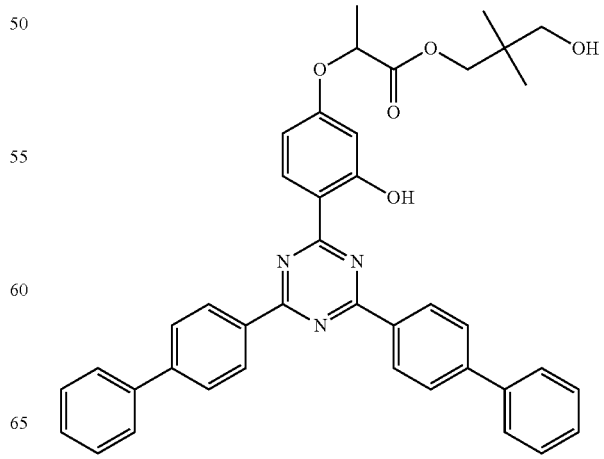

Formula (IV-3)

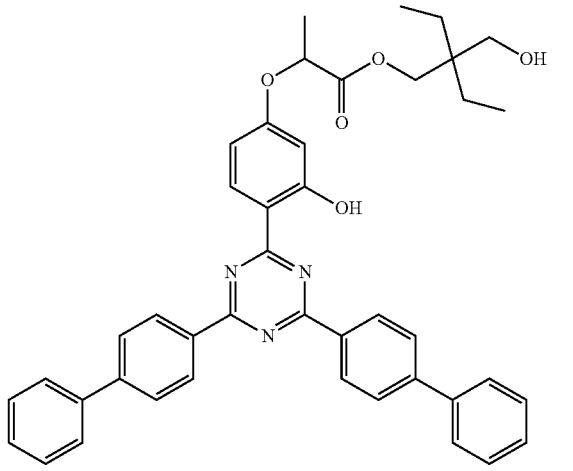

Formula (IV-4)

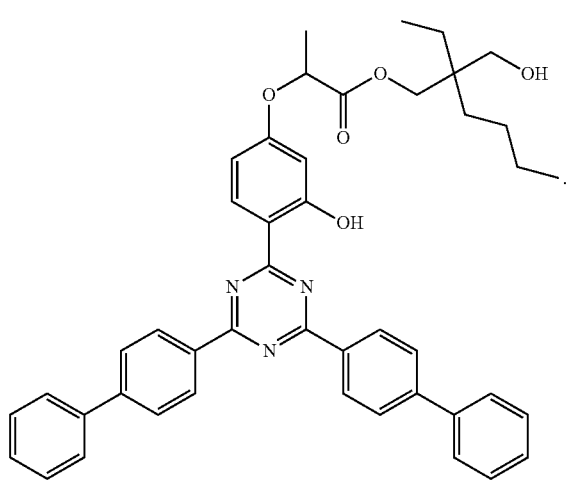

8. The process according to claim 3, wherein in step b) the isocyanate group-comprising urethane acrylate is obtainable by reacting a 1,6-hexamethylene diisocyanate isocyanurate with a hydroxyalkyl (meth)acrylate.

9. The process according to claim 3, wherein in and/or after step b) the hydroxyalkyl (meth)acrylate is selected from the group 2-hydroxyethyl (meth)acrylate, 2-hydroxypropyl (meth)acrylate, 4-hydroxybutyl (meth)acrylate and/or 3-hydroxy-2,2-dimethylpropyl (meth)acrylate.

10. A coating composition comprising the UV absorber-comprising urethane acrylate according to claim 1.

11. The coating composition according to claim 10, comprising:
   i) UV absorber-comprising urethane acrylate according to claim 1 in an amount of from 0.1 to 50 parts by weight,
   ii) from 12 to 70 parts by weight of at least one $C_2$-$C_{12}$-diol diacrylate or $C_2$-$C_{12}$-diol dimethacrylate, wherein $C_2$-$C_{12}$ represents a linear alkylene radical which can optionally be substituted by a methyl group or can be interrupted by one or more oxygen atom(s) and optionally substituted by one or more methyl group(s),
   iii) from 12 to 40 parts by weight of an alkoxylated, preferably ethoxylated, mono-, di-, tri-, tetra-, penta- or hexa-acrylate or alkoxylated, preferably ethoxylated, mono-, di-, tri-, tetra-, penta- or hexa-methacrylate,
   iv) from 0 to 40 parts by weight of at least one monomer selected from the group comprising pentaerythritol triacrylate, pentaerythritol tetraacrylate, dipentaerythritol tetraacrylate, dipentaerythritol pentaacrylate, dipentaerythritol hexaacrylate, pentaerythritol trimethacrylate, pentaerythritol tetramethacrylate, dipentaerythritol tetramethacrylate, dipentaerythritol pentamethacrylate, dipentaerythritol hexamethacrylate and possible reaction products thereof with aliphatic or aromatic diisocyanates,
   v) from 5 to 60 parts by weight of at least one further mono-, di- or tri-acrylate or mono-, di- or tri-methacrylate,
wherein the sum of the parts by weight of components i) to v) is 100 parts by weight, and the coating composition additionally comprises at least
   vi) from 0.1 to 10 parts by weight of at least one photoinitiator.

12. A method for coating a substrate, comprising the steps:
   applying the coating composition according to claim 10 to a substrate,
   curing the applied coating composition by irradiation with UV light.

13. The method according to claim 12, wherein the substrate is a thermoplastic substrate.

14. The method according to claim 12, wherein the substrate is a polycarbonate substrate.

15. A coated substrate obtained by a method according to claim 12.

* * * * *